United States Patent [19]

Berger-Lohr et al.

[11] 4,281,124
[45] Jul. 28, 1981

[54] REACTIVE QUATERNARY COMPOUNDS, THEIR PREPARATION AND THEIR USE FOR INCREASING THE AFFINITY OF ANIONIC DYESTUFFS FOR FIBRES WHICH CONTAIN NITROGEN OR HYDROXYL GROUPS

[75] Inventors: Bernd Berger-Lohr; Karl H. Schündehütte; Manfred Söll, all of Leverkusen, Fed. Rep. of Germany

[73] Assignee: Bayer Aktiengesellschaft, Leverkusen, Fed. Rep. of Germany

[21] Appl. No.: 99,116

[22] Filed: Nov. 29, 1979

[30] Foreign Application Priority Data

Dec. 14, 1978 [DE] Fed. Rep. of Germany ....... 2853881

[51] Int. Cl.$^3$ ................. C07D 251/50; C07D 251/42; C07D 295/10
[52] U.S. Cl. .................................. 544/208; 544/113; 544/209; 544/211; 544/212; 544/83
[58] Field of Search ............... 544/113, 208, 209, 211, 544/212, 218, 219, 83

[56] References Cited

U.S. PATENT DOCUMENTS

| | | |
|---|---|---|
| 2,719,156 | 9/1955 | de Benneville et al. ............. 544/113 |
| 2,725,379 | 11/1955 | Berstein et al. ....................... 544/208 |
| 3,518,266 | 6/1970 | Hausermann et al. ................ 544/113 |
| 3,732,218 | 5/1973 | Gerd et al. ............................. 544/208 |
| 4,171,955 | 10/1979 | Perrin et al. ........................... 544/208 |
| 4,180,664 | 12/1979 | Perrin et al. ........................... 544/208 |

*Primary Examiner*—John M. Ford
*Attorney, Agent, or Firm*—Sprung, Felfe, Horn, Lynch & Kramer

[57] ABSTRACT

Compounds of the formula

[structure: triazine ring with substituents E, D, B—K(+), An(−)]

wherein
E denotes a reactive substituent which can be split off,
D denotes hydrogen, optionally substituted alkyl, aryl, aralkyl, aminocarbonyl, mono- or di-alkylaminocarbonyl, optionally substituted alkoxy, alkylthio, aryloxy, arylthio, aralkoxy or aralkylthio, or a radical of the formula $$K_1^{(+)}-B_1- \quad \text{or} \quad G-N(G_1)-$$
$$An^{(-)}$$

G and G$_1$ independently of one another denote hydrogen, optionally substituted alkyl, aryl or aralkyl, or, together with N, a 5-membered or 6-membered ring,
B and B$_1$ independently of one another denote a linking member $$-X-Y-Z-Y_1-$$

wherein
X is bonded to the triazine radical and denotes oxygen, sulphur or $$-N(R)-$$

R denotes hydrogen, optionally substituted alkyl, alkenyl or aralkyl,
Y denotes $$-(C R_1 R_2)_n-,$$

n denotes a number from 0 to 4,
Z denotes an optionally substituted phenylene or naphthylene radical or the radical of the formula —CH=CH—,
Y$_1$ denotes a radical of the formula $$-(CR_1R_2)_{n1}-, \quad -O-\text{[phenylene]}-CH_2-,$$

$$-\overset{O}{\underset{\|}{C}}-CH_2-, \quad -N(R_1)-\overset{O}{\underset{\|}{C}}-CH_2-, \quad -CH_2-N(R_1)-\overset{O}{\underset{\|}{C}}-CH_2-,$$

$$-SO_2-NH-(CR_1R_2)_{n2}-, \quad -O-(CR_1R_2)_{n2}-, \quad -S-(CR_1R_2)_{n2}-,$$

$$-CH(OH)-CH_2- \quad \text{or} \quad -O-CH_2-CH(OH)-CH_2-,$$

n$_1$ denotes a number from 0 to 4, n and n$_1$ not simultaneously being 0,
n$_2$ denotes a number from 2 to 5,
R$_1$ and R$_2$ independently of one another denote hydrogen or alkyl,
K$^{(+)}$ and K$_1^{(+)}$ independently of one another denote a quaternary radical $$-\overset{(+)}{N}\begin{pmatrix}W\\W_1\\W_2\end{pmatrix}$$

W, W$_1$ and W$_2$ independently of one another denote optionally substituted alkyl, cycloalkyl, alkenyl or aralkyl, or $W_1$ and $W_2$ or $W$, $W_1$ and $W_2$, together with the nitrogen atom, denote an optionally substituted heterocyclic ring, or W denotes an amino, monoalkylamino or dialkylamino radical or a radical of the formula

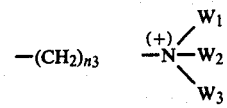

$n_3$ denotes a number from 2 to 4,
$W_3$ denotes an optionally substituted alkyl radical and $An^{(-)}$ denotes an anion, are used for increasing the affinity of anionic dyestuffs for fibres which contain nitrogen or hydroxyl groups.

4 Claims, No Drawings

REACTIVE QUATERNARY COMPOUNDS, THEIR PREPARATION AND THEIR USE FOR INCREASING THE AFFINITY OF ANIONIC DYESTUFFS FOR FIBRES WHICH CONTAIN NITROGEN OR HYDROXYL GROUPS

The present invention relates to quaternary compounds of the formula $$\begin{array}{c} E \\ N \diagup \diagdown N \\ D \diagdown \diagup B \\ N \\ \phantom{xx} K^{(+)} \end{array} \quad An^{(-)} \quad (I)$$

wherein

E denotes a reactive substituent which can be split off,

D denotes hydrogen, optionally substituted alkyl, aryl, aralkyl, aminocarbonyl, mono- or dialkylaminocarbonyl, optionally substituted alkoxy, alkylthio, aryloxy, arylthio, aralkoxy or aralkylthio, or a radical of the formula $$K_1^{(+)} - B_1 - \quad \text{or} \quad G - N - \\ An^{(-)} \phantom{xxxxxxxxxxx} | \\ \phantom{xxxxxxxxxxxxxxxxxxx} G_1$$

G and $G_1$ independently of one another denote hydrogen, optionally substituted alkyl, aryl or aralkyl, or, together with N, a 5-membered or 6-membered ring, B and $B_1$ independently of one another denote a linking member $$-X-Y-Z-Y_1-$$

wherein

X is bonded to the triazine radical and denotes oxygen, sulphur or $$\begin{array}{c} -N-, \\ | \\ R \end{array}$$

R denotes hydrogen, optionally substituted alkyl, alkenyl or aralkyl,

Y denotes $$\begin{array}{c} R_1 \\ | \\ -(C)_n- \\ | \\ R_2 \end{array}$$

n denotes a number from 0 to 4,

Z denotes an optionally substituted phenylene or naphthylene radical or the radical of the formula $-CH=CH-$, $Y_1$ denotes a radical of the formula $$-(C)_{n1}-\begin{array}{c}R_1\\|\\|\\R_2\end{array}, \quad -\!\!\bigcirc\!\!-CH_2-, \quad -O-\!\!\bigcirc\!\!-CH_2-,$$

-continued $$-\overset{O}{\underset{\|}{C}}-CH_2-, \quad -\underset{\underset{R_1}{|}}{N}-\overset{O}{\underset{\|}{C}}-CH_2-, \quad -CH_2-\underset{\underset{R_1}{|}}{N}-\overset{O}{\underset{\|}{C}}-CH_2-,$$

$$-SO_2-NH-\underset{\underset{R_2}{|}}{(\underset{\underset{R_1}{|}}{C})_{n2}}-, \quad -O-\underset{\underset{R_2}{|}}{(\underset{\underset{R_1}{|}}{C})_{n2}}-, \quad -S-\underset{\underset{R_2}{|}}{(\underset{\underset{R_1}{|}}{C})_{n2}}-,$$

$$-CH-CH_2- \quad \text{or} \quad -O-CH_2-CH-CH_2-, \\ \phantom{xx}| \phantom{xxxxxxxxxxxxxxxxxxxxxxxxxx} | \\ \phantom{x}OH \phantom{xxxxxxxxxxxxxxxxxxxxxxxxxx}OH$$

$n_1$ denotes a number from 0 to 4, n and $n_1$ not simultaneously being 0, $n_2$ denotes a number from 2 to 5, $R_1$ and $R_2$ independently of one another denote hydrogen or alkyl, $K^{(+)}$ and $K_1^{(+)}$ independently of one another denote a quaternary radical $$\begin{array}{c} W \\ (+) \diagup \\ -N-W_1 \\ \diagdown \\ W_2 \end{array}$$

W, $W_1$ and $W_2$ independently of one another denote optionally substituted alkyl, cycloalkyl, alkenyl or aralkyl, or $W_1$ and $W_2$ or W, $W_1$ and $W_2$, together with the nitrogen atom, denote an optionally substituted heterocyclic ring, or W denotes an amino, monoalkylamino or dialkylamino radical or a radical of the formula $$-(CH_2)_{n3} \quad \begin{array}{c} W_1 \\ (+) \diagup \\ -N-W_2 \\ \diagdown \\ W_3 \end{array}$$

$n_3$ denotes a number from 2 to 4, $W_3$ denotes an optionally substituted alkyl radical and $An^{(-)}$ denotes an anion, their preparation and their use for increasing the affinity of anionic dyestuffs for natural or synthetic fibre materials which contain nitrogen or hydroxyl groups.

The alkyl and alkoxy radicals have, in particular, 1-4 carbon atoms. They can be substituted by nonionic substituents, for example by halogen, such as fluorine, chlorine or bromine, or cyano, or, in the case of D, G, R, W and $W_3$, by a radical of the formula $$\begin{array}{c} R_3 \phantom{x} R_3 \\ | \phantom{xxx} | \\ -(O-CH-CH)_{n4}-O-R_4 \end{array} \quad II$$

wherein both the radicals $R_3$ represent hydrogen, or one $R_3$ represents methyl and the other represents hydrogen, $R_4$ represents hydrogen, $C_1-C_4$-alkyl, benzyl, acetyl, propionyl or benzoyl and $n_4$ represents a number from 0 to 4.

Preferred aryl radicals are phenyl radicals, and benzyl and phenylethyl are preferred aralkyl radicals. Cycloalkyl represents, in particular, cyclopentyl or cyclohexyl. The rings mentioned can be substituted, for example by halogen, such as fluorine, chlorine or bromine, $C_1-C_4$-alkyl, $C_1-C_4$-alkoxy or hydroxyl.

Alkenyl preferably represents radicals with 2-4 carbon atoms.

The radicals $W_1$ and $W_2$, together with the nitrogen atoms, can form, for example, a 5-membered or 6-membered ring, such as a pyrrolidine, piperidine, morpholine or piperazine ring. The radicals W, $W_1$ and $W_2$, together with the nitrogen atom, can form, for example, a pyridine ring. Preferred substituents of these rings are $C_1$–$C_4$-alkyl radicals.

X is to be understood, in particular, as a group of the formula

in which R represents hydrogen or $C_1$–$C_4$-alkyl, but in particular hydrogen or methyl.

Examples of Y which may be mentioned are, in addition to the direct bond, a methylene, ethylene, propylene or butylene group, but in particular a methylene group or a direct bond.

Examples of Z are a radical of the formula —CH=CH— or a phenylene or naphthylene radical which is substituted by fluorine, chlorine, bromine or hydroxyl, $C_1$–$C_4$-alkyl or $C_1$–$C_4$-alkoxy groups, but in particular an unsubstituted phenylene radical or a phenylene radical which is substituted by 1 or 2 methyl groups.

Of the linking members $Y_1$, the linking members of the formulae

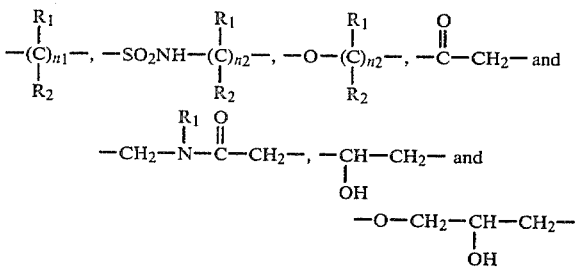

in which
$R_1$ and $R_2$ represent hydrogen or $C_1$–$C_4$-alkyl groups,
$n_1$ represents the number 1 or 2 and
$n_2$ represents the number 2 or 3,
may be mentioned in particular. However, $Y_1$ especially represents methylene or ethylene.

Examples of D which may be singled out are: methyl-, ethyl-, phenyl- and benzyl-thio, a group of the formula

in which G and $G_1$ represent hydrogen, methyl, ethyl, hydroxyethyl, phenyl or benzyl, or a group of the formula II, and in particular a group of the formula

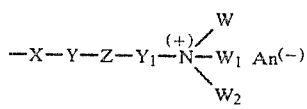

in which the radicals have the abovementioned preferred meanings.

Possible anions $An^{(-)}$ are both anions of inorganic acids and anions of organic acids. Examples which may be mentioned are: chloride, fluoride, bromide, sulphate, phosphate, tetrafluoborate and anions of aromatic and lower aliphatic carboxylic acids and sulphur acids, such as benzenesulphonate, p-toluenesulphonate, methanesulphonate, ethanesulphonate, methosulphate, ethosulphate or acetate.

The anion is generally determined by the preparation process and the method used to isolate the products (I). However, the anions can be replaced by any other desired anions in a known manner.

Reactive substituents E which can be split off are understood as substituents which can be split off under the dyeing conditions customary for reactive dyestuffs. There may be mentioned in particular: halogen, such as fluorine, chlorine or bromine, ammonium, hydrazinium, sulphonium, alkylsulphonyl, arylsulphonyl, azido ($N_3$), aryloxy, thiocyano, arylthio and sulphonic acid, halogen being particularly preferred, and especially fluorine and chlorine.

Specific examples of symmetric monohalogeno-triazine radicals which may be mentioned are: 2-amino-4-fluoro(or chloro)triazin-6-yl-, 2-alkylamino-4-fluoro(or chloro)triazin-6-yl-, such as 2-methylamino-4-fluoro(or chloro)triazin-6-yl- or 2-ethylamino- or 2-propylamino-4-fluoro(or chloro)triazin-6-yl-, 2-β-hydroxyethylamino-4-fluoro(or chloro)triazin-6-yl-, 2-di-β-hydroxyethylamino-4-fluoro(or chloro)triazin-6-yl-, 2-β-methoxyethylamino-4-fluoro(or chloro)triazin-6-yl- and the corresponding sulphuric acid half-esters, 2-dimethylamino- or 2-diethylamino-4-fluoro(or chloro)triazin-6-yl-, 2-morpholino- or 2-piperidino-4-fluoro(or chloro)triazin-6-yl-, 2-cyclohexylamino-4-fluoro(or chloro)triazin-6-yl-, 2-arylamino- and substituted arylamino-4-fluoro(or chloro)triazin-6-yl-, such as 2-phenylamino-4-fluoro(or chloro)triazin-6-yl- and 2-(o-, m- or p-carboxy- or sulphophenyl)-amino-4-fluoro(or chloro)triazin-6-yl-, 2-alkoxy-4-fluoro(or chloro)triazin-6-yl-, such as 2-methoxy- or 2-ethoxy-4-fluoro(or chloro)triazin-6-yl-, 2-(phenylsulphonylmethoxy)-4-fluoro(or chloro)triazin-6-yl-, 2-aryloxy- and substituted aryloxy-4-fluoro(or chloro)triazin-6-yl-, such as 2-phenoxy-4-fluoro(or chloro)triazin-6-yl-, 2-(p-sulphophenyl)-oxy-4-fluoro(or chloro)triazin-6-yl- and 2-(o-, m- or p-methyl- or -methoxy-phenyl)-oxy-4-fluoro(or chloro)triazin-6-yl-, 2-alkylmercapto-, 2-arylmercapto- or 2-(substituted aryl)-mercapto-4-fluoro(or chloro)triazin-6-yl-, such as 2-β-hydroxyethyl-mercapto-4-fluoro(or chloro)triazin-6-yl-, 2-phenyl-mercapto-4-fluoro(or chloro)triazin-6-yl-, 2-(4'-methylphenyl)-mercapto-4-fluoro(or chloro)triazin-6-yl- and 2-(2',4'-dinitro)-phenylmercapto-4-fluoro(or chloro)triazin-6-yl-, and 2-methyl-4-fluoro(or chloro)triazin-6-yl-.

Of the compounds of the formula (I), those of the formula

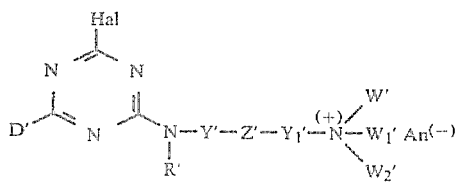

III wherein
Hal represents fluorine or chlorine,
D' represents

in which
G′ and G′₁ denote hydrogen, $C_1$–$C_4$-alkyl, phenyl or benzyl, which are optionally substituted by hydroxyl, or D′ represents

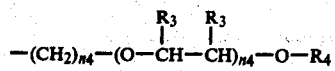

in which
the indices $n_4$ independently of one another denote a number from 0 to 4, both the radicals $R_3$ denote hydrogen or one $R_3$ denotes hydrogen and the other denotes methyl and $R_4$ denotes hydrogen or $C_1$–$C_4$-alkyl, or D′ represents

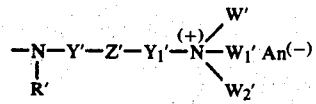

R′ represents hydrogen or $C_1$–$C_4$-alkyl, which can be substituted by

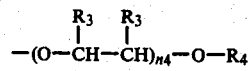

Y′ represents the formula

in which
R′₁ and R′₂ represent hydrogen or $C_1$–$C_4$-alkyl and n′ denotes 0 or 1, Z′ represents phenylene or naphthylene which is optionally substituted by fluorine, chlorine, bromine, hydroxyl, $C_1$–$C_4$-alkyl or $C_1$–$C_4$-alkoxy, Y′₁ represents a radical of the formula

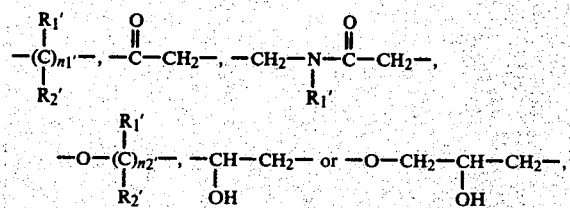

in which
n′₁ denotes 1 or 2 and
n′₂ denotes 2 or 3,

W′, W′₁ and W′₂ independently of one another represent $C_1$–$C_6$-alkyl, which can be substituted by

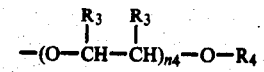

W′ also represents benzyl, amino, $C_1$–$C_4$-alkylamino or $C_1$–$C_4$-dialkylamino, or W′₁ and W′₂, together with the nitrogen atom, represent a pyrrolidine, piperidine, morpholine or piperazine ring, or W′, W′₁ and W′₂, together with the nitrogen atom, represent a pyridine ring, and $An^{(-)}$ represens an anion, are to be singled out.

Of these compounds, the bis-quaternary compounds are preferred, and of these, in turn, those in which
n′ denotes zero,
Z′ denotes phenylene which is optionally substituted by methyl and
Y′₁ denotes methylene or ethylene, are preferred.

Of the compounds of the formula (III), those of the formula

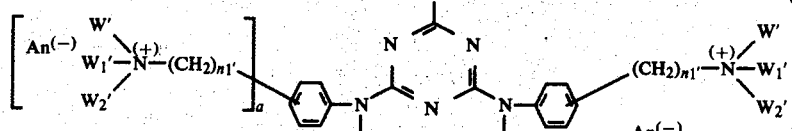

wherein
Hal, W′, W′₁, W′₂, R′, n′₁ and $An^{(-)}$ have the meaning indicated in the case of formula (III) and
a represents 0 or 1,
are preferred.

Compounds of the formula (IV) in which
R′ denotes hydrogen or methyl,
W′, W′₁ and W′₂ denote methyl, ethyl or hydroxyethyl and
n′₁ and a denote 1,
are particularly preferred.

The compounds of the formula I can be prepared by methods which are known per se, for example by processes 1a, 1b and 2:

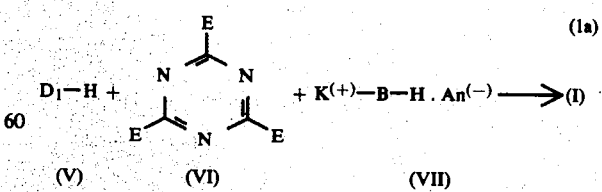

D₁ having only the meanings of D in the formula I such that D₁—H reacts with, for example, VI under the reaction conditions and HE is split off. The reactions can be carried out in any desired sequence. E represents, in particular, fluorine or chlorine.

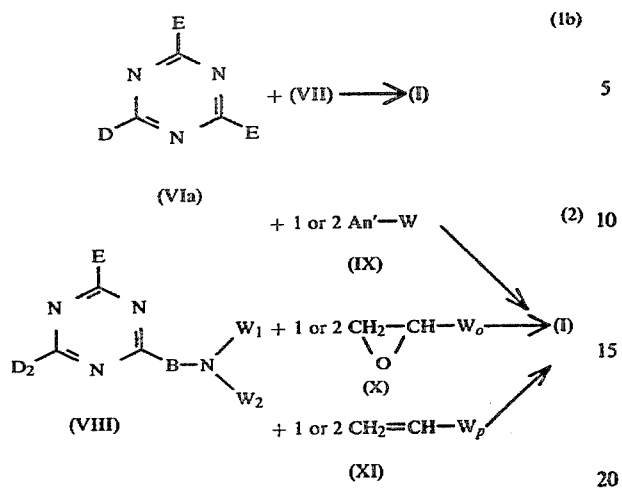

(1b)

(VIa)

(VIII)

wherein
$D_2$ has the meanings of D in the formula (I), and additionally represents $$-B_1-N\begin{matrix}W_1\\W_2\end{matrix}$$

An' represents a radical which can be split off as the anion $An^{(-)}$, $W_o$ represents hydrogen, alkyl which has 2 carbon atoms less than W, phenyl or phenoxymethyl, $W_p$ represents CN, CO—$NH_2$, COO—$R_5$ or $SO_2R_5$ and $R_5$ represents alkyl, aryl or aralkyl.

The reaction according to 1a and 1b can be carried out in an aqueous or aqueous-organic solution, preferably in a neutral or weakly acid solution, at temperatures between 0° and 80° C., preferably at 0°–40° C. The acid HE formed during the reaction is neutralised, for example with bicarbonate, sodium carbonate or sodium hydroxide solution. The compounds of the formula I are isolated from the reaction solution as solid substances or in the form of pastes. However, it is not necessary to isolate the compounds I from the reaction medium. They can also be used, for example, in the form of the solutions obtained during their preparation. Buffer substances, such as phosphates, maleates, acetates, carbonates or citrates, can be added to the reaction medium before, during or after the reaction in order to improve the stability. Examples which may be mentioned of compounds of the formula VII are:

(1) $H_2N-CH_2-CH=CH-CH_2-\overset{(+)}{N}(CH_3)_3 \ Cl^{(-)}$ (2) $H_2N-CH_2-CH=CH-CH_2-\overset{(+)}{N}(C_2H_5)_3 \ Cl^{(-)}$ (3) $H_2N-CH_2-CH=CH-CH_2-\overset{(+)}{N}(CH_3)_2(CH_2CH_2OH) \ Cl^{(-)}$ (4) $H_2N-CH_2-CH=CH-CH_2-\overset{(+)}{N}$(morpholino-CH_3) $Cl^{(-)}$ (5) $H_2N-CH_2-CH=CH-CH_2-\overset{(+)}{N}$(pyridinium) $Cl^{(-)}$ (6) $H_2N-CH_2-CH=CH-CH_2-\overset{(+)}{N}(CH_3)(C_2H_4OH)_2 \ Cl^{(-)}$ (7) $H_2N-CH_2-C_6H_4-CH_2-\overset{(+)}{N}(CH_3)_3 \ Cl^{(-)}$ (8) $H_2N-CH_2-C_6H_2(CH_3)_2-CH_2-\overset{(+)}{N}(C_2H_5)_3 \ Cl^{(-)}$ (9) $H_2N-CH_2-C_6H_4-C_6H_4-CH_2-\overset{(+)}{N}(CH_3)_3 \ Cl^{(-)}$

(10) $H_2N-CH_2-C_6H_4-O-C_6H_4-CH_2-\overset{(+)}{N}(CH_3)_3 \ Cl^{(-)}$

(11) $H_2N-C_6H_4-CH_2-\overset{(+)}{N}(CH_3)_3 \ Cl^{(-)} \ oder \ CH_3SO_4^{(-)}$

(12) $H_2N-C_6H_4-CH_2-\overset{(+)}{N}(CH_3)_3 \ Cl^{(-)} \ oder \ CH_3SO_4^{(-)}$

(13) $H_2N-C_6H_4-CH_2-\overset{(+)}{N}(CH_3)_2(C_2H_4OH) \ Cl^{(-)}$

(14) $H_2N-C_6H_4-CH_2-CH_2-\overset{(+)}{N}(CH_3)_3 \ CH_3SO_4^{(-)} \ oder \ Cl^{(-)}$

(15) $H(CH_3)N-CH_2-C_6H_4-CH_2-\overset{(+)}{N}(CH_3)_3 \ Cl^{(-)}$

(16) $H(C_2H_5)N-CH_2-CH=CH-CH_2-\overset{(+)}{N}(C_2H_5)_3 \ Cl^{(-)}$

(17) $H_2N-C_6H_4-O-CH_2-CH_2-\overset{(+)}{N}(CH_3)_3 \ Cl^{(-)}$

(18) $H_2N-C_6H_4-S-CH_2-CH_2-\overset{(+)}{N}(CH_3)_3 \ Cl^{(-)}$

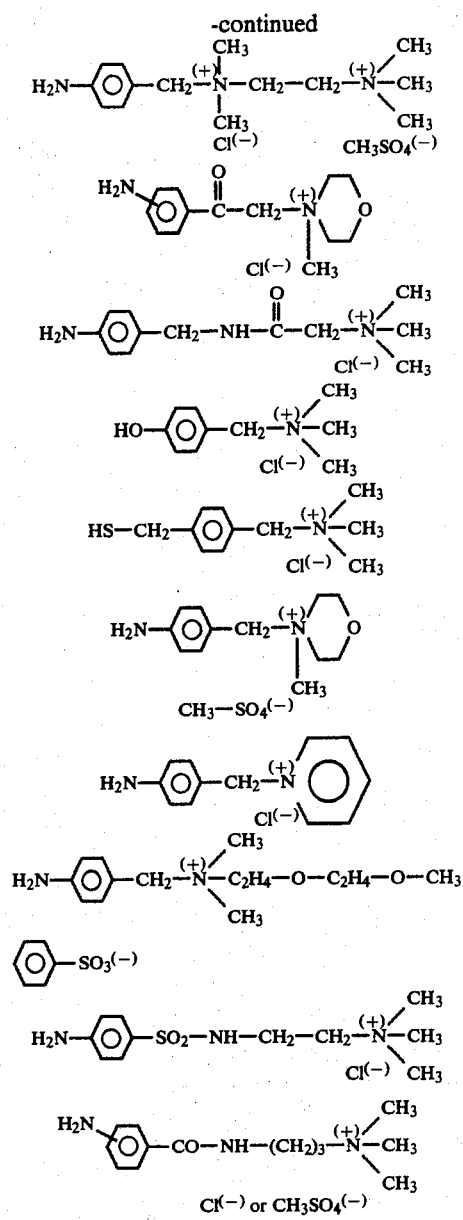

Of the large number of compounds VI and VIa available, the following may be mentioned here as examples: symmetric trihalogeno-triazines, such as 2,4,6-trifluoro-triazine, 2-chloro-4,6-difluoro-triazine, 2,4-dichloro-6-fluoro-triazine, cyanuric chloride, cyanuric bromide, symmetric dihalogeno-monoamino- and mono- and di-substituted amino-triazines, such as 2,6-difluoro(or dichloro)-4-aminotriazine, 2,6-difluoro(or dichloro)-4-methylaminotriazine, 2,6-difluoro(or dichloro)-4-ethylaminotriazine, 2,6-difluoro(or dichloro)-4-dimethylaminotriazine, 2,6-difluoro(or dichloro)-4-diethylaminotriazine, 2,6-difluoro(or dichloro)-4-hydroxyethylaminotriazine, 2,6-difluoro(or dichloro)-4-phenylamino-triazine, 2,6-difluoro(or dichloro)-4-(o-, m- or p-sulphophenyl)-aminotriazine and 2,6-difluoro(or dichloro)-4-(2',3'-, 2',4'-, 3',4'- or 3',5'-disulphophenyl)-aminotriazine, symmetric dihalogeno-alkoxy- and aryloxy-triazines, such as 2,6-difluoro(or dichloro)-4-methoxy-triazine, 2,6-difuloro(or dichloro)-4-ethoxy-triazine, 2,6-difluoro(or dichloro)-4-iso-propoxy-triazine, 2,6-difluoro(or dichloro)-4-(2-methoxy-ethoxy)-triazine, 2,6-difluoro(or dichloro)-4-phenoxy-triazine and 2,6-difluoro(or dichloro)-4-(o-, m- or p-sulphophenyl)-oxytriazine, and symmetric dihalogenoalkylmercapto- and -arylmercapto-triazines, such as 2,6-difluoro(or dichloro)-4-ethylmercapto-triazine, 2,6-difluoro (or dichloro)-4-phenylmercapto-triazine and 2,6-difluoro(or dichloro)-4-(p-methylphenyl)-mercapto-triazine, it also being possible for the two reactive halogen substituents in the 2-position and in the 6-position to differ from one another, such as, for example, in the case of the 2-fluoro-6-chloro- or 2-chloro-6-fluoro-triazin-4-yl radical.

Examples of further reactive components of the triazine series, with reactive sulphonyl substituents, are 2,4-bis-methylsulphonyl-1,3,5-triazine, 2,4-bis-methylsulphonyl-6-(3'-sulphophenylamino)-1,3,5-triazine, 2,4-bis-methylsulphonyl-6-N-methylanilino-1,3,5-triazine and 2,4,6-tris-phenylsulphonyl-1,3,5-triazine.

Quaternising agents IX, X and XI which may be mentioned are: alkyl halides, aralkyl halides, cycloalkyl halides, dialkyl sulphates, alkyl esters of arylsulphonic acids and other esters of strong mineral acids and organic sulphonic acids with preferably lower alcohols. In the presence of acids, it is also possible to use acrylic acid and derivatives thereof and epoxides as alkylating agents. The quaternising agents can be further substituted. Examples are: dimethyl sulphate, diethyl sulphate, methyl chloride, methyl bromide, methyl iodide, methyl sulphate, ethyl bromide, n-propyl bromide, n-butyl bromide, allyl chloride, methyl chloroacetate and bromoacetate, methyl and ethyl methanesulphonate, ethylene chlorohydrin, chloroacetonitrile, benzyl chloride, phenylethyl chloride, phenoxy-β-chloroethane, butenyl chloride, chloramine, O-methylsulphonylhydroxylamine, O-mesitylenesulphonylhydroxylamine, N,N-dimethylchloramine, hydroxylamino-O-sulphonic acid, acrylonitrile, ethylene oxide and propylene oxide.

The compounds of the formula (I) to be used according to the invention can be applied, to the fibre material to be dyed, in a pre-treatment process, or they are used together with the anionic dyestuffs in one bath. They can also be applied to finished dyeings and prints in an after-treatment process. In the case of a pre-treatment process, the fibre material treated with the compounds of the formula (I) is then dyed from a long liquor in the manner customary for the particular dyestuffs. However, it is also possible to dye the material from a short liquor.

Pre-treatment is effected by impregnating or printing the material with aqueous padding liquors or printing pastes which contain, in addition to the compounds (I) in amounts of 20–150 g, preferably 40–100 g, per liter of padding liquor or printing paste, the alkali necessary for the chemical reaction with the fibre material, for example sodium bicarbonate, sodium hydroxide or, preferably, sodium carbonate. The fibre material thus impregnated is pressed off to a liquor pick-up of 60–100%, preferably 70–90%, of the weight of fibre and is subjected to a heat treatment, with or without intermediate drying. This heat treatment can be steaming for a short time, for example a steam treatment at 102° to 120° C. for 3 to 10 minutes, or treatment with dry heat for a short time, for example at 120° to 150° C. for 2 to 10 minutes; during this heat treatment, the compounds (I) react with the fibre material, a chemical bond being formed. However, the reaction with the fibre material can also be effected by a cold pad-batch process by rolling up the impregnated and pressed-off material and keeping it at room temperature for 4 to 24 hours. In that case, it is necessary to ensure, by wrapping with water-impermeable material, that no water can evaporate.

The batch time can be reduced to one to four hours by increasing the batch temperature from room temperature to 60°–80° C.

When the compounds (I) are used together with dyestuffs in one bath, padding liquors or printing pastes are prepared which contain, in addition to the compounds (I) in amounts of 20–150 g, preferably 40–100 g, per liter of padding liquor or per kg of printing paste, the anionic dyestuffs and also the padding auxiliaries and wetting agents customary in dyeing, the thickeners and reducing agents customary in textile printing and the necessary alkaline agent, for example sodium bicarbonate, sodium carbonate or sodium hydroxide. Subsequent fixing is effected in the customary manner by a steam, dry heat or cold pad-batch treatment.

For the after-treatment of finished dyeings or prints, the compounds (I) are employed, in aqueous solution, in amounts of 0.1–8%, preferably 1–5%, relative to the substrate. The solutions contain 1–5 ml/l of sodium hydroxide (50% strength). The finished dyeings are treated in these solutions at temperatures of 20°–80° C., preferably 20°–40° C., for 10–60 minutes.

For the after-treatment, it is also possible to prepare padding liquors which also contain, in addition to the compounds having the composition (I) in amounts of 20–150 g, preferably 40–100 g, per liter of padding liquor, the padding auxiliaries and wetting agents customary in dyeing and the necessary alkaline agents, for example sodium bicarbonate, sodium carbonate or sodium hydroxide. Subsequent sequent fixing in this case is effected by a steam, dry heat or cold pad-batch treatment.

A surprisingly great improvement in the colour fastness, in particular fastness to water, perspiration and washing, compared with the colour fastness of customary dyeings and prints obtained with anionic dyestuffs is achieved with the aid of the compounds (I) according to the invention. Deeper dyeings and prints are also produced, since the rinsing and soaping after-treatments do not lead to detachment of the dyestuffs from the fibre material, as is otherwise the case for untreated dyeings and prints.

The compounds (I) are used on textile material of natural cellulose, such as cotton or linen, or regenerated cellulose, such as viscose staple, rayon or high wet-modulus fibres; these fibre materials can be either by themselves or as mixtures with synthetic fibre materials, for example mixtures with polyester, polyamide or polyacrylonitrile.

Compounds having the composition (I) can be used for the pre-treatment, one-bath treatment and after-treatment of materials on which dyeings and prints are obtained with those dyestuffs such as are listed, for example, as acid dyestuffs in the Colour Index, 3rd edition (1971), volume 1 on pages 1001–1561, and as direct dyestuffs in volume 2 on pages 2005–2477.

Compared with the known cationic after-treatment agents for direct dyestuffs, the advantages of the compounds having the composition (I) are that the dyeings obtained on material which has been subjected to pre-treatment, one-bath treatment or after-treatment with these compounds have a significantly improved fastness to washing, even at elevated washing temperatures, for example at 60° C., and even at 95° C. The fastness to light is not adversely affected and only slight changes in colour shade, or no changes in colour shade, can be detected.

EXAMPLE 1

Trimethyl-(4-(3)-aminobenzyl)-ammonium methosulphate (mixture)

126 g (1 mol) of dimethyl sulphate are added dropwise to a solution of 150 g (1 mol) of a technical grade mixture of dimethyl-(4- and 3-aminobenzyl)-amine in 1,000 ml of acetone at 20°–30° C. The colourless reaction product which has precipitated is filtered off and, after drying in vacuo, about 262 g (95% of theory) of a mixture of the compounds of the formulae

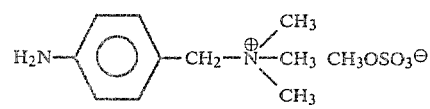

and

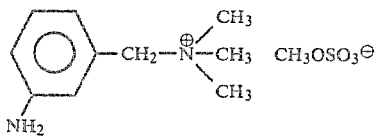

are obtained.

EXAMPLE 2

Trimethyl-(3-aminobenzyl)-ammonium methosulphate 126 g (1 mol) of dimethyl sulphate are added dropwise to a solution of 150 g (1 mol) of dimethyl-(3-aminobenzyl)-amine in 1,000 ml of acetone at 20°–30° C. The colourless reaction product which has precipitated is filtered off and, after drying in vacuo, about 260 g (94% of theory) of the compound of the formula

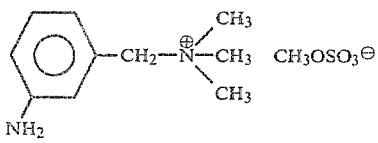

(melting point: 145° C.) are obtained. The compound can be recrystallised from isopropanol.

Synthesis of the reactive salts of the formula I:

EXAMPLE 3

67.5 g (0.5 mol) of 2,4,6-trifluorotriazine ar added dropwise to a solution of 276 g (1 mol) of trimethyl(4-(3)-aminobenzyl)-ammonium methosulphate (mixture) in 500 ml of water at 0°–5° C., whilst stirring. A pH value of 5–7 is maintained by adding sodium hydroxide solution, sodium carbonate solution or bicarbonate. The mixture is then allowed to warm to 20° C. and is subsequently stirred for about 4 hours, the pH value being kept at 7 with sodium hydroxide solution, sodium carbonate solution or bicarbonate, and if necessary the mixture is filtered. A solution which contains about 300–320 g of a mixture of the compounds of the formulae

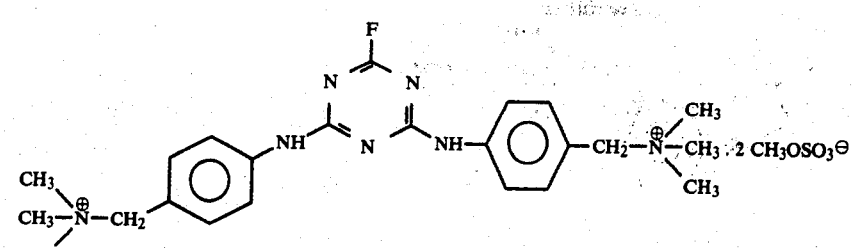

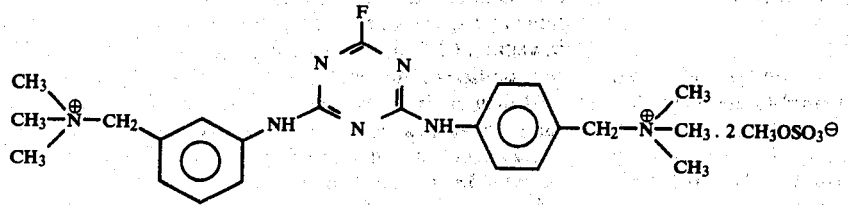

and

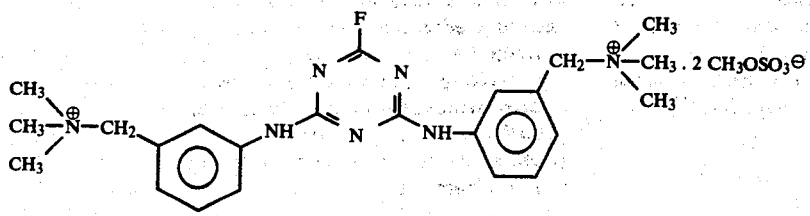

is obtained. The aqueous solution can be concentrated at 20° C. in vacuo, and a paste which contains a mixture of these compounds is obtained; however, it is also possible to use the aqueous solution directly.

EXAMPLE 4

126 g (1 mol) of dimethyl sulphate are added dropwise to a solution of a technical grade mixture of 150 g (1 mol) of dimethyl-(4- and 3-aminobenzyl)-amine in 300 ml of water at 0°-20° C., whilst stirring. When the exothermic reaction has subsided, the mixture is stirred for a further 2 hours and 67.5 g (0.5 mol) of 2,4,6-trifluorotriazine are then added at 0°-5° C., a pH value of 5-7 being maintained by adding sodium hydroxide solution, bicarbonate or sodium carbonate solution. The mixture is then allowed to warm to 20° C. and is subsequently stirred for about 4 hours, the pH value being kept at 7 with sodium hydroxide solution, bicarbonate or sodium carbonate solution, and if necessary the mixture is filtered. The resulting solution contains about 300–320 g of a mixture of the compounds of the formulae

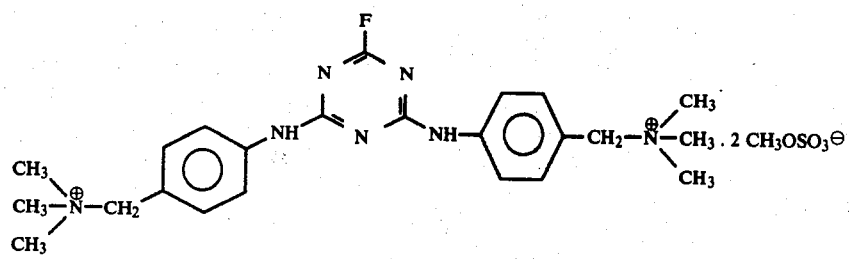

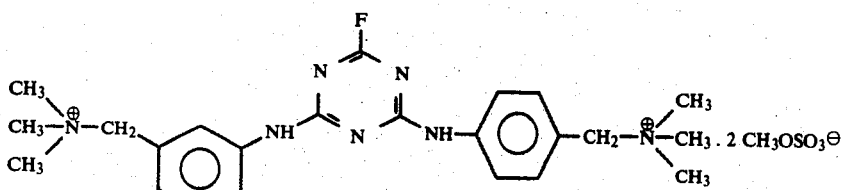

and

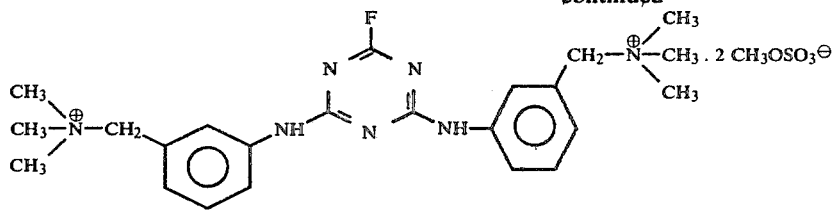

The solution can be used directly in this form.

EXAMPLE 5

92.25 g (0.5 mol) of cyanuric chloride are added to a solution of 276 g (1 mol) of trimethyl-(3-aminobenzyl-)ammonium methosulphate in 500 ml of water at 5°–10° C., whilst stirring. A pH value of 5–7 is maintained by adding sodium hydroxide solution, bicarbonate or sodium carbonate solution. The mixture is then stirred at 20° C. until a clear solution is obtained, which is then warmed to 30° C., the pH value in each case being kept at 7 with sodium hydroxide solution, bicarbonate or sodium carbonate solution, and if necessary the solution is filtered. A solution which contains about 300–330 g of the compound of the formula

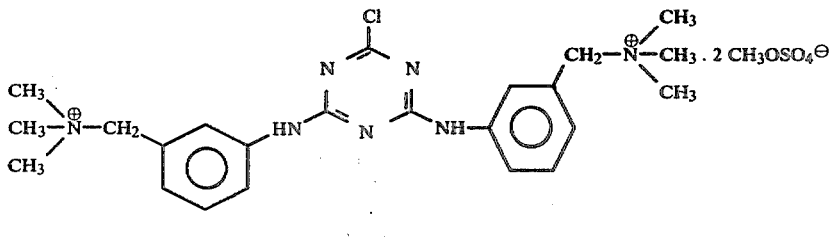

is obtained. This solution can be used directly, or diluted as required, or concentrated by stripping off water in vacuo at 20°–30° C. This also applies, for example, to the solutions obtained according to Examples 3 and 4.

However, it is also possible, for example, to isolate the reactive quaternary compounds obtained according to this example and according to Examples 3 and 4, for example by a procedure in which the water is stripped off in vacuo at 20°–30° C., the residue is eluted with methanol, the undissolved inorganic salts are filtered off and the methanolic solution is concentrated.

In contrast, it is simpler and more economical to use the resulting aqueous solution directly, if appropriate diluted or concentrated as described above.

Other examples of compounds of the general formula I which can be obtained by a procedure analogous to that in Examples 3 to 5 are listed in the Table below.

| Example No. | Compound VII | Compound VI or VIa | Compound I |
|---|---|---|---|
| 6 | | | |
| 7 | | | |
| 8 | | | |
| 9 | | | |
| 10 | | | |

| Example No. | Compound VII | Compound VI or VIa | Compound I |
|---|---|---|---|
| 11 | | | |
| 12 | | | |
| 13 | | | |
| 14 | | | |

EXAMPLE 15

A dyeing is produced on a piece of cotton fabric using 3% of C.I. Direct Blue 225 (Colour Index (1971) 3rd edition, volume 2) from an aqueous dye liquor by the dyeing procedure customary for these dyestuffs and the fabric is rinsed and dried. This dyes fabric is impregnated on a dye padder, at room temperature, with a solution which contains 50 g of the compound of Example 3 or 4 and 20 g of sodium carbonate per liter and is pressed off such that the liquor pick-up of the dyed fabric is about 80%. The material is then dried in a drying cabinet at 60°–70° C. and subsequently steamed at 102° C. for 8 minutes. On rinsing, which now follows, at room temperature and at 60°–70° C. for 5 minutes in each case, the rinsing baths remain colourless, and on subsequent treatment in distilled water at 95° C. the treatment liquor is only slightly stained over a period of 20 minutes.

A blue dyeing with very good fastness to light, water, perspiration and washing is obtained.

A blue dyeing with the advantageous properties mentioned is also obtained if C.I. Direct Blue 151 (=C.I. No. 24,175) is used as the dyestuff.

EXAMPLE 16

A piece of cotton fabric which has been dyed with 3% of C.I. Direct Blue 225 is treated in the course of 25 minutes, in a liquor ratio of 1:30 and at 20°–25° C., in a fresh bath which contains, relative to the weight of the cotton, 4% of the compound of Example 3 or 4 and 2 ml/l of 50% strength sodium hydroxide solution. The fabric is then rinsed in cold water and in water heated to 60° C., and is dried. A blue dyeing with very good fastness to light, water, perspiration and washing is obtained.

Similar results are obtained if, instead of 4% of the compound of Example 3 or 4, 4% of the compound of Example 8, 8% of the compound of Example 11, 4% of the compound of Example 13 or 7% of the compound of Example 14 are used.

EXAMPLE 17

An aqueous solution which contains 60 g of the compound of Example 5 and 30 g of the dyestuff C.I. Direct Orange 76 (=C.I. No. 40,270) per liter is prepared. 15 g of sodium carbonate are added to this solution and a piece of cotton fabric is impregnated with the solution and pressed off such that a liquor pick-up of 80% results. The fabric thus treated is dried at 60° C. and heated to 150° C. for 3 minutes. On subsequent rinsing out in water at room temperature and at 60° C., for 5 minutes in each case, and on treating the fabric in boiling water for 20 minutes, no staining of the treatment liquors takes place.

The scarlet dyeing thus obtained is distinguished by good fastness to light, water, perspiration and washing.

Similar results are obtained if, instead of 60 g of the compound of Example 5, 80 g of the compound of Example 6, 80 g of the compound of Example 7, 70 g of the compound of Example 8 or 80 g of the compound of Example 14 are used.

We claim:

1. A compound of the formula $$\begin{array}{c} Hal \\ | \\ N \diagup \diagdown N \\ \| \quad \| \\ D'\diagdown N \diagup N-Y'-Z'-Y_1'-\overset{(+)}{N}\diagup W' \\ | \qquad \qquad \qquad \diagdown W_2' \\ R' \end{array} \quad An^{(-)}$$

wherein

Hal is fluorine or chlorine,

D' is $$G'-N-, \quad -(CH_2)_{n4}-(O-\overset{R_3}{\underset{|}{CH}}-\overset{R_3}{\underset{|}{CH}})_{n4}-O-R_4 \quad or$$
$$\underset{G_1'}{|}$$

$$-N-Y'-Z'-Y_1'-\overset{(+)}{N}\diagup^{W'}_{W_2'} \quad An^{(-)},$$
$$\underset{R'}{|}$$

G' and G'$_1$ each independently is hydrogen, $C_1$–$C_4$-alkyl, phenyl or benzyl, which are optionally substituted by hydroxyl, n$_4$ each independently is a number from 0 to 4, one of the radicals R$_3$ is hydrogen and the other is hydrogen or methyl, R$_4$ is hydrogen or $C_1$–$C_4$-alkyl, R' is hydrogen or $C_1$–$C_4$-alkyl which can be substituted by $$-(O-\overset{R_3}{\underset{|}{CH}}-\overset{R_3}{\underset{|}{CH}})_{n4}-O-R_4$$

Y' is $$\begin{array}{c} R_1' \\ | \\ (C)_n- \\ | \\ R_2' \end{array},$$

R'$_1$ and R'$_2$ each independently is hydrogen or $C_1$–$C_4$-alkyl, n is 0 or 1, Z' is phenylene or naphthylene which is optionally substituted by fluorine, chlorine, bromine, hydroxyl, $C_1$–$C_4$-alkyl or $C_1$–$C_4$-alkoxy, Y'$_1$ is a radical of the formula $$-\overset{R_1'}{\underset{R_2'}{\underset{|}{(C)_{n1'}}}}-, \quad -\overset{O}{\overset{\|}{C}}-CH_2-, \quad -CH_2-N-\overset{O}{\overset{\|}{C}}-CH_2-,$$

$$-O-\overset{R_1'}{\underset{R_2'}{\underset{|}{(C)_{n2'}}}}-, \quad -\underset{OH}{\underset{|}{CH}}-CH_2- \text{ or } -O-CH_2-\underset{OH}{\underset{|}{CH}}-CH_2-,$$

n'$_1$ is 1 or 2, n'$_2$ is 2 or 3,

W', W'$_1$ and W'$_2$ each independently is $C_1$–$C_6$-alkyl which can be substituted by

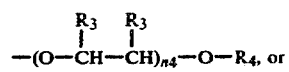

W' also may be benzyl, amino, $C_1$-$C_4$-alkylamino or $C_1$-$C_4$-dialkylamino, or W'$_1$ and W'$_2$, together with the nitrogen atom, may form a pyrrolidine, piperidine, morpholine or piperazine ring, or W', W'$_1$ and W'$_2$, together with the nitrogen atom, may form a pyridine ring, and $An^{(-)}$ is an anion.

2. A compound according to claim 1, wherein
n' is zero,
Z' is phenylene which is optionally substituted by methyl and
Y'$_1$ is methylene or ethylene.

3. A compound according to claim 1 of the formula

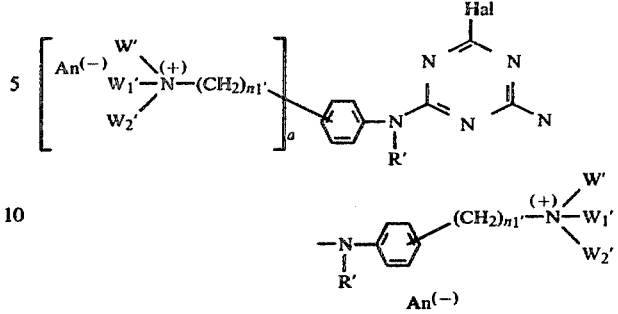

wherein a is 0 or 1.

4. A compound according to claim 3, wherein
R' is hydrogen or methyl,
W', W'$_1$ and W'$_2$ each independently is ethyl or hydroxyethyl, and
n'$_1$ and a are 1.

* * * * *